United States Patent [19]

Miller et al.

[11] Patent Number: 4,757,055

[45] Date of Patent: Jul. 12, 1988

[54] METHOD FOR SELECTIVELY CONTROLLING UNWANTED EXPRESSION OR FUNCTION OF FOREIGN NUCLEIC ACIDS IN ANIMAL OR MAMMALIAN CELLS

[75] Inventors: Paul S. Miller, Baltimore; Paul O. P. Ts'O, Lutherville, both of Md.

[73] Assignee: The Johns Hopkins University, Baltimore, Md.

[21] Appl. No.: 604,919

[22] Filed: Apr. 27, 1984

Related U.S. Application Data

[63] Continuation-in-part of Ser. No. 363,230, Mar. 29, 1982, Pat. No. 4,511,713, which is a continuation-in-part of Ser. No. 206,297, Nov. 12, 1980, Pat. No. 4,469,863.

[51] Int. Cl.4 .................... A61K 31/70; A61K 31/665
[52] U.S. Cl. ......................................... 514/44; 514/47; 514/51
[58] Field of Search ...................... 536/29, 28; 514/44, 514/47, 51

[56] References Cited

U.S. PATENT DOCUMENTS

| | | | |
|---|---|---|---|
| 4,469,863 | 9/1984 | Ts'O et al. ............................ | 536/27 |
| 4,507,433 | 3/1985 | Miller et al. .......................... | 536/29 |
| 4,511,713 | 4/1985 | Miller et al. .......................... | 536/27 |

OTHER PUBLICATIONS

Miller et al., "Interrelationship Among Aging, Cancer and Differentiation", Pullman et al. (eds), D. Reidel Publishing Co., 1985, pp. 207–219.

Smith et al., "Proc. Natl. Acad. Sci.", U.S.A., vol. 83, pp. 2787–2791, May 1986.

Agris et al., Biochemistry, in press, 1986.

Primary Examiner—J. R. Brown
Assistant Examiner—Jenny Tou
Attorney, Agent, or Firm—Cushman, Darby & Cushman

[57] ABSTRACT

A process for selectively controlling or interfering with the effect or function of foreign nucleic acid in the presence of otherwise normal living cells which comprises determining the base sequence for said nucleic acid and binding the said nucleic acid with an appropriately prepared nonionic oligonucleoside alkyl or arylphosphonate analogue which is complementary to the indicated sequence of the foreign nucleic acid.

4 Claims, 2 Drawing Sheets

METHOD FOR SELECTIVELY CONTROLLING UNWANTED EXPRESSION OR FUNCTION OF FOREIGN NUCLEIC ACIDS IN ANIMAL OR MAMMALIAN CELLS

RELATED APPLICATION

The present application is a continuation-in-part of U.S. application Ser. No. 363,230, filed Mar. 29, 1982, now U.S. Pat. No. 4,511,713 which is a continuation-in-part of U.S. application Ser. No. 206,297, filed Nov. 12, 1980, now U.S. Pat. No. 4,469,863. The contents of these two applications are incorporated herein by reference.

The present invention is concerned with the use of certain nonionic oligonucleotides to selectively control undesired nucleic acid within or in the presence of mammal or animal cells without affecting the normal function of such cells.

BACKGROUND OF THE INVENTION

It is well known that nucleic acids, i.e. deoxy ribonucleic acid (DNA) and ribonucleic acid (RNA) are essential building blocks in living cells. These acids are high molecular weight polymers which are made up of many "nucleotide" units, each such nucleotide unit being composed of a base (a purine or pyrimidine), a sugar (which is either ribose or deoxyribose) and a molecule of phosphoric acid. DNA contains deoxyribose and the bases adenine, guanine, cytosine and thymine (which may be represented as A, G, C and T, respectively). RNA contains ribose instead of deoxyribose and uracil (U) in place of thymine.

The nucleotide units in DNA and RNA are assembled in definite linear sequences which determine specific biological responses. In the normal mammalian cell, DNA replicates itself and also causes the formation of RNA molecules whose nucleotides sequences carry certain information possessed by the DNA. Thus, the RNA may serve as a messenger (mRNA) for the DNA in order to perform certain functions. The RNA also serve to synthesize protein.

According to the well known Watson-Crick model, each nucleic acid molecule consists of two polynucleotide strands coiled about a common axis. The resulting double helix is loosely held together by hydrogen bonds between complementary base pairs in each strand. In the case of DNA, for example, it appears that hydrogen bonds are formed only between adenine (A) and thymine (T) and between guanine (G) and cytosine (C). Hence adrenine (A) and thymine (T) are viewed as complementary bases which bind to each other as A—T. The same is true for guanine (G) and cytosine (C), as G—C.

In a single polynucleotide strand, any sequence of nucleotides is possible. However, once the order of bases in one strand is specified, the exact sequence in the other chain is simultaneously determined due to indicated base pairing. Accordingly, each strand in a DNA or RNA molecule is the complement of the other and each molecule contains two strands. In replication of DNA, the two strands act as a template for the formation of a new chain with complementary nucleotide sequence. The net result is the production of two new strands complementary to each other and each identical with one of the original strands. These may replicate further DNA or RNA, and as programmed in the system involved.

It is known that bacteria and viruses contain nucleic acids, every bacteria and virus species being characterized by its own special nucleic acid sequence. Bacteria contain very large amounts of both DNA and RNA while viruses generally contain only one kind of nucleic acid, either DNA or RNA, but not both. In any case, as noted, the nucleic acid for any particular bacteria or virus species has a characteristic sequence which, stated simply, can be viewed as a "fingerprint" of that particular species.

When a virus invades a normally functioning mammalian cell, the viral nucleic acids (hereinafter called "foreign" nucleic acid for ease of reference) tend to replicate thus, in effect, reproducing more viral nucleic acids and virus and in one way or another destroy or undesirably affect the function of the infected cell and the cell host. Bacterial cells can replicate, grow, and excrete toxic substances in the presence of mammalian cells. The nucleic acids of the bacteria, both DNA and RNA, function independently of the mammalian cellular nucleic acids and may thus be considered "foreign" nucleic acids. There is also the possibility of malfunctioning mammalian cells wherein the cellular nucleic acids or portions of the cellular nucleic acids are replicated or produced in an aberrant manner with consequent undesirable effects on the cell. For example undesired or aberrant cellular DNA and particularly RNA molecules might be produced which could lead to the production of unwanted or malfunctioning proteins. For present purposes, the existance or the expression of nucleic acid resulting from any such malfunctioning is also called "foreign nucleic acid" to differentiate from the DNA and RNA existent or normally expressed in the normally functioning cell.

OBJECTS OF THE INVENTION

The principal object of the invention is to provide a way of controlling foreign nucleic acid in the presence of living mammalian or animal cells without undesirably affecting these cells and their normal function. A more specific object of the invention is to provide a process whereby foreign nucleic acid in a cell may be bound so that it cannot interfere with the normal function of the cell. Other objects will also be hereinafter apparent.

BROAD DESCRIPTION OF THE INVENTION

Broadly speaking, the objects of the invention are realized by a method which involves the determination of the relevant sequence or sequences of any foreign nucleic acid in or adjacent to an otherwise normal mammalian cell and this sequence or sequences will be bound or interfered with by a nonionic deoxyribooligonucleoside alkyl- or arylphosphonate analogue, or a nonionic 2-O-alkyl- or 2'-O-arylribooligonucleoside alkyd- or arylphosphonate analogue, or a nonionic 2'-O-halogenoribooligonucleoside alkyl- or arylphosphone analogue, preferably a methylphosphonate, which possess a nucleic acid base sequence complementary to the indicated foreign nucleic acid sequence or sequences. These nonionic, complementary oligonucleotide analogs will be synthesized specifically and consequently serve to bind the foreign nucleic acid into an essentially inactive state so that it cannot replicate itself and/or function in an undesired manner as the case may be.

The oligonucleoside methylphosphonates, or similar alkyl or aryl phosphonates, contemplated for use herein are chemically synthesized analogues of nucleic acid which are specifically designed to have the following unique properties: (1) they can easily pass through the membrances of living cells and can thus enter the cell's interior; (2) they are resistant to degradation or hydrolysis by nuclease enzymes found within the cells, and thus have a relatively long lifetime within the cell; and (3) they can strongly-interact with complementary nucleic acids or polynucleotides found inside the cell to form stable complexes therewith. By interacting with a selected complementary foreign nucleic acid in a cell or adjacent to a cell whether the nucleic acid is derived from bacteria, virus or malfunction, the phosphonate can selectively inhibit the function or expression of that particular nucleic acid without disturbing the function or expression of other nucleic acids present in the cell. This selectivity potentially allows one to prevent the growth of viruses, bacterial cells, transformed cells, pathological cells or tumor cells in the presence of normal, helathy cells. In other words, the invention comtemplates the use of the indicated alkyl or aryl phosphonate analogues to selectively block or interfere with the single stranded regions of predetermined foreign nucleic acid sequences and thereby inhibit the function or expression of the foreign nucleic acid involved. Because of the unique selectivity of the analogues, based on sequence complementarity, the normal functioning of the cell is not affected. Each virus, bacteria, and malfunctioning cellular nucleic acid has its own distinctive "fingerprint" nucleic acid sequence. Hence once this sequence is determined over a reasonable length of the foreign nucleic acid chain, it is possible to prepare its complementary phosphonate analogue which then binds itself to the foreign nucleic acid and prevents it from replicating, directing protein synthesis and/or otherwise functioning in an undesirable manner. The length of the nucleic acid chain which needs to be determined and the corresponding length of the complementary phosphonate nucleotide analogue or oligonucleotide which needs to be used for present purposes, will vary depending on the circumstances. It is believed, however, that an analogue which is complementary with respect to a 3-20, preferably 9-12, base sequence of the foreign nucleic acid will usually be adequate to effectively control or interfere with the foreign nucleic acid.

PRIOR PUBLICATIONS

It has previously been disclosed that nucleic acids are potential target regions for base-printing interactions with complementary nucleotides for the purpose of probing and regulating the sequence-function relationship of nucleic acids in both biochemical and cellular systems. Thus, deoxyribooligonucleotides complementary to the reiterated 3'- and 5'-terminal nucleotides of Rous sarcoma virus 35S RNA have been shown to inhibit the translation of the RNA in a cell-free system as well as the virus production in chicken fibroblast tissue cultures (see papers by Stephenson et al, Proc. Natl. Acad. Sci. USA, 75, 285–288 and by Zamecnik et al in the same publication at pages 280–284). It was not demonstrated, however, that the complementary deoxyribooligonucleotides entered the chicken fibroblast cells.

Previous reports have also described the interaction of nonionic, oligonucleotide ethyl phosphotriesters with transfer RNA (Miller et al, 1974, Biochemistry, 4887) and the effects of these analogues on cell-free aminoacylation of tRNA (Barrett et al, 1974, Biochemistry 13, 4898). A trinucleotide analogue, $G_p{}^m(Et)G_p{}^m(Et)U$ has also been described as being taken up by mammalian cells in culture and as having specific inhibitory effects on cellular protein synthesis and cell growth (Miller et al, 1977, Biochemistry 16, 1988–1996). The inhibitory effect disclosed by Miller et al for the indicated trinucleotide analogue was, however, only transitory due apparent to degradation of the analogue by cell enzymes.

Certain dinucleoside methylphosphonate analogues of dinucleotides are described by Miller et al in Fed. Proc. Abst. 36, 695 (1977). This abstract also discloses that because these analogues enter mammalian cells, form specific complexes with complementary sequences, and are stable, they are useful as probes and regulators of nucleic acid function within living cells. The abstract does not, however, disclose the present concept of using the analogues to selectively bind foreign nucleic acid in a cell without affecting the normal function of the cell, indicating the nucleic acid conventionally present therein.

It is also noted that the synthesis of a series of nonionic oligonucleotide analogues, namely, dideoxyribonucleoside methyl phosphonates, suitable for use herein, is described by Miller et al, (1979) Biochemistry 18, 5134–5143. These analogues have an isosteric, 3'-5'-linked methylphosphonate group which replaces the normal phosphodiester linkage of nucleic acids. Physical studies by ultraviolet, circular dichroism, and nuclear magnetic resonance spectroscopic techniques indicate that the conformation of these analogues is similar to those of the corresponding phosphodiesters and that the analogues form stable complexes with complementary polynucleotides (see again Miller et al, (1979), Biochemistry 18, 5134–5143 and Kan et al, (1980), Biochemistry 19, 2122).

DESCRIPTION OF THE DRAWINGS

FIG. 1 illustrates a representative deoxyribooligonucleoside methylphosphonate analogue suitable for use herein while

DETAILED DESCRIPTION OF THE INVENTION

Oligonucleoside methylphosphonates or like alkyl or arylphosphonates for use herein include those described in U.S. application Ser. No. 206,297 and in the above referenced power by Miller et al (1979) Biochemistry 18, 5134–5143. These nonionic oligonucleotide analogues may be prepared in the manner disclosed in said application and paper and also by other methods which will be understood by those in the art.

Before any such analogue is prepared or used, however, it is essential to determine the sequence of the foreign nucleic acid which is to be bound or interfered by the methylphosphonate analogue or equivalent thereof. Such sequence can be determined in conventional fashion using methods and apparatus currently available to those in the art. The sequences for some viral, bacterial and mammalian cellular nucleic acids are already well established but in other cases it will be necessary to determine these sequences, or at least an essential portion thereof, at the outset.

As noted earlier herein, it appears that the length of the nucleic acid sequence which is determined can be varied. Additionally, it appears that the positioning of the determined sequence in terms of the overall nucleic acid chain can also be varied although, generally speaking, it may be preferable to utilize a sequence at or near the 5' end of the chain or the middle thereof rather than the end as related to the function of the foreign nucleic acid in replication, expression, or translation processes. Normally the sequence determined, and the complementary analogue, should cover at least 3 adjacent bases and preferably 9–15 such bases. This may be varied, however, depending on other factors, e.g. whether a virus or bacteria or a malfunctioning cell is involved and the nature and effect of the nucleic acid of concern.

Once the sequence of the nucleic acid is determined the appropriate complementary alkyl or arylphosphonate analogue, preferably the methylphosphonate analogue, is prepared. This may be accomplished, as disclosed in Ser. No. 206,297, by, for example, condensing or esterifying a selected nucleoside which has a 3'—OH group and a protected 5'—OH group with an alkyl or aryl phosphonic acid, the resulting product then being condensed with another nucleoside which has a protected 3'—OH group and a reactive 5'—OH group. The esterification reactions are continued with sequential reaction involving the phosphonic acid group of the preceding product and a selected nucleoside until the desired oligonucleoside is obtained after which protecting group or groups are removed to give the desired oligonucleoside alkyl or arylphosphonate analogue wherein the nucleoside units are linked by isosteric 3'-5' alkyl or arylphosphonate groups. These latter groups are preferably methylphosphonate linking groups although if desired the methyl substituent may be replaced by other alkyl or aryl groups or substituents.

Figure 1:
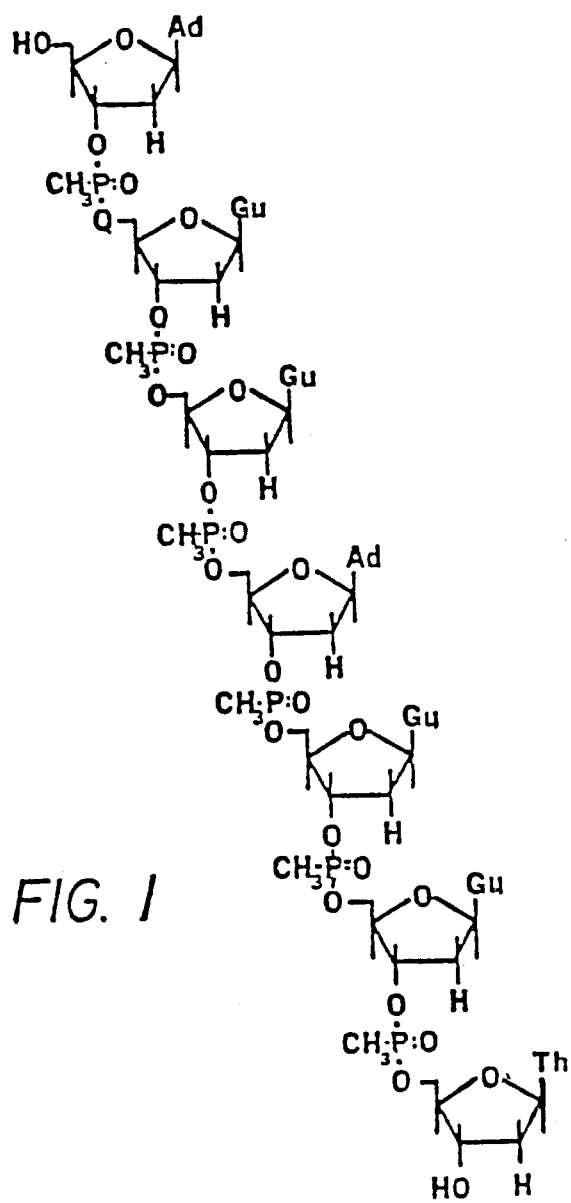

FIG. 1 shows a representative oligonucleotide analogue suitable for use according to the invention, the analogue in this case comprising a hepta deoxyribonucleoside methylphosphonate. The deoxyribonucleoside units which are shown occur in the order: deoxadenosine-deoxyguanosine-deoxyquanosine-deoxyadenosine-deoxyguanosine-deoxyquanosine-thymidine, these being linked at a 3'→5' manner by methylphosphonate groups. This analogue may be more simply illustrated as d-$(A_pG_pG_p)_2T$ where p stands for the 3'-5' linked methylphosphonate group. According to the invention, this analogue would be used to bind or interfere with a foreign nucleic acid with the complementary base sequence D-$A_pC_pC_pT_pC_pC_pT$. As noted, it is essential for the phosphonate analogue to have a sequence complementary to the foreign nucleic acid involved or targeted. Thus, for example, in the case of a virus DNA where the sequence may be —A—T—C—G, the analogue must have the complementary sequence of —T—A—G—C— so that the sequences are bound together according to the Watson-Crick theory as follows:

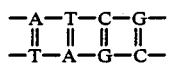

Likewise in the case where mRNA having the sequence —UAGC— is concerned, the complementary analogue would be —ATCG—, such analogue serving to prevent, interfere or reduce translation of the mRNA to protein.

While the invention is exemplified below using certain nonionic oligonucleoside methylphosphonate analogues against specific types of nucleic acid, it will be appreciated that the invention is of broader application and is intended for use in countering what is termed herein for convenience "foreign nucleic acid" from virus, bacteria or malfunctioning cells to selectively control or interfere with the virus, bacteria or malfunctioning cells, in the presence of normal healthy living mammalian or animal cells without affecting the normal function of these cells. For example, virus nucleic acid within a cell may tend to direct the synthesis of viral nucleic acids and proteins and thus create more virus. Determination of the relevant virus nucleic acid sequence or sequences involved in these processes permits one to make complementary oligonucleoside alkyl or arylphosphonate which can be introduced into the cell and will then bind to the virus nucleic acid sequence or sequences and prevent, interfere with or control its undesirable function. The alkyl and arylphosphonate analogues contemplated for use herein have a number of unique physical and biochemical properties including (a) the ability to form stable complexes with complementary polynucleotides, (b) the ability to penetrate the membranes or boundaries of living cells, and (c) resistance by hydrolysis by cellular nucleases or by chemical means. They, therefore, nicely lend themselves for administration and use in controlling foreign nucleic acid in or adjacent to living cells.

The invention is illustrated by the following examples, it being noted that the symbols used to represent protected nucleosides and oligonucleoside methylphosphonates follow the IUPAC-IUB Commission on Biochemical Nomenclature (1976) recommendations.

EXAMPLE 1

This example describes the preparation and use of a series of oligonucleoside methylphosphonates whose base sequences are complementary to the anticodon loops of $tRNA^{Lys}$ species and to the —ACCA—OH amino acid accepting stem of tRNA.

The example demonstrates that these oligodeoxyadenosine methylphosphonates form stable, triple-stranded complexes with both poly(U) and poly(dT). The following test results are also shown: The analogues selectively inhibit cell-free aminoacylation of $tRNA^{Lys}_{E.\ coli}$ but have no effect on aminoacylation of $tRNA^{Lys}_{rabbit}$. The extent of inhibition is temperature dependent and parallels the ability of the oligomer to bind to poly(U). This indicates that inhibition occurs as a result of oligomer binding to the —UUUU— anticodon loop of $tRNA^{Lys}_{E.\ Coli}$. The failure of the oligodeoxyadenosine methylphosphonates to inhibit $tRNA^{Lys}_{rabbit}$ aminoacrylation indicates that there is a difference between the structure of $tRNA^{Lys}$ or its interaction with aminoacyl synthetase in the Escherichia coli and rabbit systems. The oligodeoxyadenosine analogues also effectively inhibit polyphenylalanine synthesis in cell-free translation systems derived from both E. coli and rabbit reticulocytes. The extent of inhibition parallels the $T_m$ values of the oligo(A) phosphonate-poly(U) complexes and indicates that the inhibition is a consequence of complex formation with the poly(U) message. It is also shown that tritium-labeled oligodeoxyribonucleoside methylphosphonates with a chain length of up to nine nucleotidyl units are taken up intact by mammalian cells in culture. All the oligomer analogues tested inhibited, to various extents, colony formation by bacterial, hamster, and human tumor cells in culture.

MATERIALS USED

Commercially available nucleosides (P-L Biochemicals) were employed. These were checked for purity by paper chromatography before use.

N-Benzoyldeoxyadenosine, N-isobutyryl-deoxyguanosine, their 5'-O-dimethoxytrityl derivatives, and 5'-O-(methoxytrityl)thymidine were prepared according to published procedures (see Schaller et al, JACS 85, 3821 (1963) and Buchi et al, J. Mol. Biol. 72, 251 (1972)).

d-[(MeO)$_2$Tr]bzApbzApCNEt, d-[(MeO)$_2$Tr]-bzApbzAOAc, d-[(MeO)Tr]TpTpCNEt, d-ApT, d-Ap[$^3$H]T, d-TpT, and d-Tp[$^3$H]T were synthesized by procedures previously described (Miller et al, 1979, Biochemistry 18, 5134).

Commercially available dimethyl methylphosphonate and benzenesulfonic acid were used without further purification. Hydracrylonitrile was dried over 4-Å molecular sieves. Methylphosphonic acid dipyridinium salt and mesitylenesulfonyl tetrazolide (MST), the latter used as condensing agent, were prepared as previously described (see again Miller et al, 1979, Biochemistry 18, 5134).

Anhydrous pyridine was prepared by refluxing reagent-grade pyridine (3 L) with chlorosulfonic acid (40 mL) for 7 h, followed by distillation onto sodium hydroxide pellets (40 g). After being refluxed for 7 h, the pyridine was distilled onto 4-Å molecular sieves and stored in the dark.

Silica gel column chromatography was carried out by using Baker 3405 silica gel (60–200 mesh). Thin-layer silica gel chromatography (TLC) was performed on E. Merck silica gel 60 F$_{254}$ plastic-backed TLC sheets (0.2 mm thick). High-pressure liquid chromatography (LC) was carried out by using a Laboratory Data Control instrument on columns (2.1 mm×1 m) packed with HC Pellosil. The columns were eluted with a linear gradient (40 mL total) of chloroform to 20% (v/v) methanol in chloroform at a flow rate of 1 mL/min. Ultraviolet spectra were recorded on a Cary 14 or a Varian 219 ultraviolet spectrophotometer with a temperature-controlled cell compartment. The following extinction coefficients (260 nm) were used: dT, 9100; d-[(MeO)Tr]T, 10200; d-[(MeO)$_2$Tr]bzA, 12500; d-bzA, 10600; d-[(MeO)$_2$Tr]ibuG, 17400; d-ibuG, 16700. Paper chromatography was carried out on Whatman 3 MM paper using solvent A: 2-propanol-concentrated ammonium hydroxide-water (7:1:2 v/v).

Preparation of d-[MeO$_2$Tr]ibuGpCNEt d[(MeO)$_2$Tr]ibuG (12 g, 18.7 mmol) and the pyriidinium salt of methylphosphonic acid (21 mmol) were dried by evaporation with anhydrous pyridine (4×20 mL) and the residue in 40 mL of pyridine was treated with 2,4,6-triisopropylbenzenesulfonyl chloride (12.7 g, 42 mmol) for 8 h at room temperature. Hydracrylonitrile (4.5 g, 63 mmol) and 2,4,6-triisopropylbenzenesulfonyl chloride (0.61 g, 2 mmol) were added and the reaction mixture was kept at room temperature. After 2 days the reaction mixture was poured into 500 mL of ice-cold 5% NaHCO$_3$ solution. The solution was extracted with ethyl acetate (2×250 mL) and the combined extracts were dried over anhydrous Na$_2$SO$_4$. Examination of the extract by TLC showed the presence of both d-[(MeO)$_2$Tr]ibuGpCNEt (R$_f$ 0.31, silica gel TLC, 10% MeOH—CHCl$_3$) and d-ibuGpCNEt (R$_f$ 0.14, silica gel TLC, 10% MeOH—CHCl$_3$). After concentration the ethyl acetate extract was chromatographed on silica gel (4×35 cm) by using ether (1 L) and a 0–20% linear gradient of methanol in chloroform (1.6 L total) as solvents. d-[(MeO)$_2$Tr]ibuGpCNEt (2.75 mmol) was obtained in 15% yield while d-ibuGpCNEt (2.46 mmol) was obtained in 13% yield. Additional d-[(MeO)$_2$Tr]ibuGp (3.69 mmol, 20%) was obtained from the aqueous bicarbonate solution after extraction with chloroform (2×200 mL).

Preparation of Protected Oligonucleoside Methylphosphonates

These were prepared using the general procedures described for the preparation of dinucleoside methylphosphonates in Miller et al, 1979, Biochemistry 18, 5134, and Ser. No. 206,297. Suitably protected monomers or oligomer blocks carrying a 3'-terminal methylphosphonate group were condensed with protected mono- or oligonucleotides bearing a free 5'-hydroxyl group. Mesitylenesulfonyl tetrazolide was used as the condensing agent.

The specific conditions used in the condensation reactions and the yields obtained after silica gel column chromatography are given in Table I. The ultraviolet spectroscopic characteristics and the mobilities of the protected oligonucleotides on silica gel TLC and silica gel high-pressure LC are given in Table II.

TABLE II

Ultraviolet Spectral Properties and Chromatographic Mobilities of Protected Oligodeoxyribonucleoxide Methylphosphonates

| oligomer | UV spectra$^a$ | | | | | silica gel TLCR$_f{}^b$ in MeOH—CHCl$_2$ | | | | silica gel HPLC$^c$ retention time (min) |
|---|---|---|---|---|---|---|---|---|---|---|
| | $\lambda_{max}$ (nm) | $\lambda_{min}$ (nm) | $\epsilon_{240}/\epsilon_{225}$ calcd | obsd | $\epsilon_{240}/\epsilon_{225}$ calcd | obsd | 5% | 10% | 15% | 20% | |
| d-[(MeO)tr]TpTpTpTpCNEt | 265<br>235 sh | 243 | 1.34 | 1.31 | 1.55 | 1.64 | — | — | 0.08 | 0.29 | — |
| d-[(MeO)tr]Tp(Tp)$_6$TpCNEt | 265 | 243 | 1.75 | 0.92 | 1.57 | 1.56 | — | 0.00 | — | 0.13 | — |
| d-[(MeO)$_2$Tr]ibuGpibuGpCNEt | 238<br>253<br>260<br>280 | 225<br>245<br>256<br>270 | 1.19 | 1.05 | 1.33 | 1.32 | — | 0.16 | — | — | 19.2 |
| d-[(MeO)$_2$Tr]ibuGpbzAOAc | 235<br>278 | 256 | 0.82 | 0.75 | 0.88 | 0.87 | — | 0.29 | — | — | 12.3 |
| d-ibuGpbzAOAc | 260<br>280 | 239<br>267 | 1.63 | 1.27 | 0.90 | 0.90 | — | 0.18<br>0.14 | — | — | 15.5<br>17.6 |
| d-[(MeO)$_2$Tr]ibuGpibuGpTOAc | 240 sh<br>260<br>275 sh | 228 | 1.34 | 1.51 | 1.38 | 1.45 | — | 0.18 | — | — | 16.0 |
| d-[(MeO)$_2$Tr]bzApbzApbzAOAc | 234 | 227 | 0.66 | 0.61 | 0.59 | 0.59 | — | 0.41 | 0.55 | — | 13.4 |

TABLE II-continued

Ultraviolet Spectral Properties and Chromatographic Mobilities of Protected Oligodeoxyribonucleoxide Methylphosphonates

| oligomer | UV spectra[a] | | | | | silica gel TLCR$_f$[b] in MeOH—CHCl$_2$ | | | | silica gel HPLC[c] retention time (min) |
|---|---|---|---|---|---|---|---|---|---|---|
| | $\lambda_{max}$ (nm) | $\lambda_{min}$ (nm) | $\epsilon_{240}/\epsilon_{225}$ calcd | obsd | $\epsilon_{240}/\epsilon_{225}$ calcd obsd | 5% | 10% | 15% | 20% | |
| | 280 | 255 | | | | | 0.38 | 0.53 | | 14.3 |
| d-(MeO)$_2$TrbzApbzApbzpbzAOAc | 233 sh 280 | 253 | 0.71 | 0.60 | 0.59  0.60 | — | — | 0.31 | — | 19.3 |
| d-[(MeO)$_2$Tr]bzApbzApibuGpbzAOAc | 235 sh 280 | 255 | 0.89 | 0.74 | 0.73  0.75 | — | 0.15 | 0.44 | — | 23.8 |

[a]Measured in 95% EtOH.
[b]E. Merck silica gel 160 F$_{254}$ sheets 0.2 mm thick.
[c]HC Pellosil (2.1 mm × 1 m); 0–20% methanol in chloroform: 1 mL/min: 40-mL total volume.

Preparation of Oligonucleoside Methylphosphonates

The protecting groups were removed from the blocked oligonucleoside methylphosphonates by using conditions described by Miller et al. In the case of the dA-containing oligomers, the N-benzoyl groups were removed by treatment with hydrazine. The remaining 3′—O—acetyl and 5′—O—dimethoxythrityl groups were removed by sequential treatment with ammonium hydroxide and 80% acetic acid. The oligomers were purified by preparative paper chromatrography using solvent A. For the $^3$H-labeled oligothymidine methylphosphonates, d-(Tp)$_n$[$^3$H]T, the condensation reactions containing d-[(MeO)Tr](Tp)$_n$ plus [$^3$H]TOAc were run on 0.01 (n=1) and 0.005 (n=4 and 8) mmol scales while d-GpGp[$^3$H]T was prepared on a 0.012-mmol scale. The protecting groups were removed without isolation of the protected $^3$H-labeled oligomers and the entire reaction mixture was chromatographed on paper. The oligonucleoside methylphosphonates were eluted from the paper with 50% aqueous ethanol. The ethanol solutions were passed through DEAE-cellulose columns (0.5 × 1 cm) and stored at 0° C. The following overall yields were obtained: d-(Tp)$_n$[$^3$H]T (n=1, 41%; n=4, 22%; n=8, 17%) and d-GpGp[$^3$H]T (15%). The UV spectral properties and chromatographic mobilities of the oligonucleoside methylphosphonates are given in Table III.

TABLE III

Spectral Properties and Chromatographic Mobilities of Oligodeoxyribonucleoside Methylphosphonates

| oligomer | UV spectra[a] | | | | paper chromatography[b] R$_f$ solvent A |
|---|---|---|---|---|---|
| | $\lambda_{max}$ (nm) | $\lambda_{min}$ (nm) | $\epsilon_{240}/\epsilon_{225}$ | $\lambda_{max}$ | |
| d-GpGpT[c] | 257 270 sh | 230 | 1.45 | 33.4 × 10$^3$ | 0.31 |
| d-ApApA | 258 | 232 | 4.27 | 39.0 × 10$^3$ | 0.29 |
| d-ApApApA | 258 | 230 | 3.77 | 50.4 × 10$^3$ | 0.11 |
| d-ApApGpA | 258 | 227 | 3.03 | 50.3 × 10$^3$ | 0.11 |
| d-Tp[$^3$H]T | 267 | 235 | 1.53 | | 0.59 |
| d-(Tp)$_4$[$^3$H]T | 266 | 235 | 1.49 | | 0.21 |
| d-(Tp)$_2$[$^3$H]T | 266 | 235 | 1.56 | | 0.17 |

[a]Measured in water, pH 7.0.
[b]R$_f$ of pT = 0.11.
[c]The UV spectrum is similar in that of d-GpGpT (Miller et al. 1974).

For use in the tests described hereinafter, aliquots containing the required amount of oligomer were evaporated to dryness, and the oligomer was dissolved in the buffer used in the particular test.

Interaction of Oligodeoxyadenylate Methylphosphonates with Polynucleotides

Continuous variation experiments and melting experiments were carried out as described by Miller et al, 1971, JACS 93, 6657. The extinction coefficients of the oligomers were determined by comparing the absorption of a solution of the oligomer in water at pH 7.0 to the absorption of the same solution at pH 1.0. The oligomer extinction coefficient was calculated from the observed hyperchromicity of the oligomer at pH 1.0 by using the following extinction coefficients: dA, pH 1.0, 14.1 × 10$^3$; dG, pH 1.0, 12.3 × 10$^3$. The molar extinction coefficient of poly(U) is 9.2 × 10$^3$ (265 nm) and of poly(dT) is 8.52 × 10$^3$ (264 nm).

Cell-Free Aminoacylation (1) *E. coli* System. Unfractionated *Escherichia coli* tRNA (obtained from Schwarz/Mann) and unfractionated *E. coli* aminoacyl synthetase (Miles Laboratories, Inc.) were used. Reactions were run in 60 µL of buffer containing 100 mM Tris-HCl, pH 7.4, 10 mM Mg(OAc)$_2$, 5 mM KCl, 2 mM ATP, 4µM $^3$H-labeled amino acid, 1.8 µM tRNA$_{E.\ coli}$ and 0–100 µM. oligonucleotide, following the procedure of Barrett et al (Biochemistry 13, 4898, (1974)).

Reactions were initiated by addition of 4 µg of aminoacyl synthetase. Aliquots (10 µL) were removed at various times and added to 1 mL cold 10% trichloroacetic acid and the resulting precipitate was filtered on Whatman G/F filters. After being washed with four (1 mL) portions of 2N HCl and four (1 mL) portions of 95% ETOH, the filters were dried and counted in 7 mL of New England Nuclear 949 scintillation mixture.

(2) Rabbit Reticulocyte System. A rabbit reticulocyte cell-free translation system prepared by New England Nuclear (lot no. J1157AW) was used. Reactions were run in 12.5 µL of buffer containing 1 µL of the translation mixture, 79 mM potassium acetate, 0.6 mM magnesium acetate, 57 µM [$^3$H]lysine, and 50 µM oligomer. The reactions were initiated by addition of 5 µL of reticulocyte lysate and were assayed as described for the E. coli system.

Cell-Free Protein Synthesis (1) *E. coli* System. A cell-free protein synthesizing system was isolated from *E. coli* B cells (S-30) according to the procedure of Nirenberg (1963), Methods Enzymol. 6, 17). The system incorporates 300 pmol of [$^3$H]phenylalanine/mg of S-30 protein after 15-min incubation at 37° C. when poly(U) is used as a message.

(2) Rabbit Reticulocyte. The reticulocyte translation system prepared by New England Nuclear was used. For the translation of globin mRNA, the reactions were run in 12.5 μL of buffer containing 1 μL of the translation mixture, 0.10 μg of globin mRNA (Miles Laboratories). 79 mM potassium actate, 0.2 mM magnesium acetate, 0–50 μM oligomer, and 20.5 μM [$^3$H]leucine. For the translation of poly(U), the reactions were run in 12.5 μL of buffer containing 1 μL of the translation mixture, 120 mM potassium acetate, 0.8 mM magnesium acetate, 367 μM poly(U), 0–200 μM oligomer (base concentration), and 32 μM [$^3$H]phenylalanine. Reactions were initiated by addition of 5 μL of reticulocyte lysate. Aliquots (2 μL) were removed at various times and added to 1.0 mL of bovine serum albumin (100 μg) solution. The protein was precipitated by heating with 1 mL of 10% trichloroacetic acid at 70° C., filtered on G/F filters, and counted in 7 mL of Betafluor.

Uptake of Oligodeoxyribonucleoside Methylphosphonates

The uptake of d-Ap[$^3$H]T, d-GpGp[$^3$H]T, and d-(Tp)$_n$[$^3$H]T by transformed Syrian hamster fibroblasts was determined as described by Miller et al, Biochemistry 16, 1988 (1977).

Effects of Oligodeoxyribonucleoside Methylphosphonates on Colony Formation (1) *E. coli*. *E. coli* B was grown in M-9 medium supplemented with glucose (36 g/L) and 1% casamino acids. The cells were harvested in mid-log phase and resuspended in 50 μL of fresh medium containing 0–160 μM oligomer at a final cell density of 1×10$^4$ cells/mL. The cells were incubated for 1 h at 37° C. and then diluted with 0.9 mL of medium. A 0.8-mL aliquot was added to 2.5 mL of 0.8% Bactoagar at 45° C. This solution was quickly poured onto a 100-mm plate containing solid 1.2% Bactoagar. After solidification, the plates were incubated overnight at 37° C. and the resulting colonies were counted.

(2) Transformed Syrian Hamster Embryonic Fibroblasts (BP-6) and Transformed Human Fibroblasts (HTB1080). Colony formation by the fibroblasts in the presence of the methylphosphonate analogues was carried out as described by Miller et al, Biochemistry 16, 1988 (1977).

The detailed results of the tests described above were as follows:

Interaction of Oligodeoxyribonucleoside Methylphosphonates with Complementary Polynucleotides.

Table IV summarizes the melting temperatures of complexes formed between oligodeoxyadenosine methylphosphonates and poly(U) or poly(dT). For comparison, the melting temperatures of complexes formed by oligodeoxyribo- and oligoribo-adenosines are included. Each oligomer forms a triple-stranded complex with a stoichiometry of 2U:1A or 2T:1A. The melting temperatures increase as the chain length of the oligonucleotide increases. For a given chain length, the complexes formed by the methylphosphonate analogues melt at higher temperatures than those formed by the natural diester oligomers. With the exception of r-ApApApA, the complexes formed by the oligomers with poly(dT) have slightly higher melting temperatures than the corresponding complexes formed with poly(U).

The interaction of d-GpGp[$^3$H]T with unfractionated tRNA$_{E.\ coli}$ was measured by equilibrium dialysis. The apparent association constants at 0°, 22°, and 37° C. are 1100M$^{-1}$, 200M$^{-1}$, and 100M$^{-1}$, respectively. These binding constants are much lower than those of the 2'-O-methylribooligonucleotide ethyl phosphotriester, G$^m$p(Et)G$^m$p(Et)[$^3$H]U, which are 9300M$^{-1}$ (0° C.), 1900M$^{-1}$ (22° C.), and 2000M$^{-1}$ (37° C.).

TABLE IV

Interaction of Oligonucleoside Methylphosphonates with Complementary Polynucleotides[a]

| oligomer | T$_m$ with poly (U) (2U:1A)(°C.) | T$_m$ with poly (dT) (2T:1A)(°C.) |
|---|---|---|
| d-ApA: isomer 1 | 15.4 | 18.7 |
| isomer 2 | 19.8 | 18.4 |
| d-ApApA | 33.0 | 36.8 |
| d-ApApApA | 43.0 | 44.5 |
| d-ApA | 7.0 | 9.2 |
| d-ApApApA | 32.0 | 35.5 |
| r-ApApApA | 36.2 | 2.4 |

[a]5 · 10$^1$ M total [nucleotide]10 mM Tris. and 10 mM MgCl$_{22}$ pH 7.5.

Effect of Oligodeoxyribonucleoside Methylphosphonates on Cell-Free Aminoacylation of tRNA The effects of selected oligodeoxyribonucleoside methylphosphonates on aminoacylation of unfractionated tRNA$_{E.\ coli}$ are shown in Table V. Three amino acids were tested at various temperatures. The deoxyadenosine-containing analogues which are complementary to the —UUUU— sequence of the anticodon of tRNA$_{E.\ coli}$$^{Lys}$ have the largest inhibitory effect on aminoacylation of tRNA$_{E.\ coli}$$^{Lys}$. The percent inhibition increases with increasing chain length and decreases with increasing temperature. Inhibition by d-ApApGpA and by the diesters d-ApApApA and r-ApApApA is less than that exhibited by d-ApApApA. In contrast to their behavior with tRNA$_{E.\ coli}$$^{Lys}$, neither the methylphosphonates, d-ApApApA and d-ApApGpA, nor the phosphodiesters, d-ApApApA and r-ApApApA, had any inhibitory effect on tRNA$_{rabbit}$$^{Lys}$ in the rabbit reticulocyte cell-free system.

TABLE V

Effects of Oligonucleoside Methylphosphonates on Aminoacylation in an *E. coli* Cell-Free System

| | % inhibition[b] | | | | |
|---|---|---|---|---|---|
| | Phe. | Len. | Lys | | |
| Oligomer[a] | 0° C. | 0° C. | 0° C. | 22° C. | 37° C. |
| d-ApA | 6 | 0 | 7 | | |
| d-ApApA | 9 | 0 | 62 | 15 | 0 |
| d-ApApApA | 9 | 12 | 88 | 40 | 16 |
| d-ApApGpA | 12 | 12 | 35 | 0 | |
| d-GpGpT | 31 | 5 | 34 | 9 | 15 |
| dGpGpT (400 μM) | 23 | | | | |
| d-ApApApA | 0 | 7 | 71[c] | 15[c] | |

TABLE V-continued
Effects of Oligonucleoside Methylphosphonates on Aminoacylation in an *E. coli* Cell-Free System

| | % inhibition[b] | | | | |
|---|---|---|---|---|---|
| | Phe. | Len. | Lys | | |
| Oligomer[a] | 0° C. | 0° C. | 0° C. | 22° C. | 37° C. |
| r-ApApApA | | | | 78[d] | 17[d] |

[a][oligomer] = 50 μM.
[b][tRNA$_{E.\ coli}$] = 2 μM.
[c][oligomer] = 100 μM.
[d][oligomer] = 125 μM.

Effects of Oligodeoxyribonucleoside Methylphosphonates on Cell-Free Protein Synthesis The ability of deoxyadenosine-containing oligonucleoside methylphosphonates to inhibit polypeptide synthesis in cell-free systems directed by synthetic and natural messages was tested. The results of these experiments are given in Table VI. Poly(U)-directed phenylalanine incorporation and poly(A)-directed lysine incorporation are both inhibited by oligodeoxyadenosine methylphosphonates and diesters in the *E. coli* system at 22° C. The percent inhibition increases with oligomer chain length and is greater for polyphenylalanine synthesis. The methylphosphonate analogues are more effective inhibitors than either d-ApApApA or r-ApApApA at the same concentration. Although both the oligodeoxyadenosine methylphosphonates and the phosphodiesters inhibit translation of poly(U) in the rabbit reticulocyte system, no effect on the translation of globin message was observed. As in the case of the *E. coli* system, inhibition of phenylalanine incorporation increased with oligomer chain length and was greater for the methylphosphonate analogues than for the diesters.

TABLE VI
Effects of Oligonucleoside Methylphosphates on Bacterial and MamMalian Cell-Free Protein Synthesis at 22° C.

| | % INHIBITION | | | |
|---|---|---|---|---|
| | *E. coli* | | | rabbit reticulocyte globin mRNA directed[c] |
| oligomer | poly (U) directed[a] | poly (A) directed[b] | poly (U) directed[a] | |
| d-ApA | 20 | 10 | | |
| d-ApApA | 84 | 30 | 81 | |
| d-ApApApA | 100 | 65 | 77 | 0 |
| d-ApApGpA | 22 | | | 0 |
| d-ApApApA | 13 | 19 | 18 | 0 |
| r-ApApApA | 18 | 17 | 85 | 0 |

[a][poly (U)] = 360 μM in U; [oligomer] = 175–200 μM in base.
[b][poly (A)] = 300 μM in A; [oligomer] = 175–200 μM in base.
[c][oligomer] = 200 μM in base.

Uptake of Oligodeoxyribonucleoside Methylphosphonates by Mammalian Cells

Figure 2:
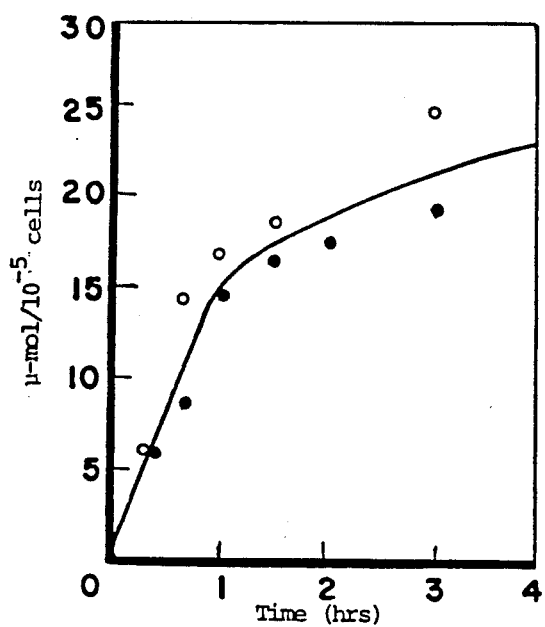
FIGS. 2 and 3 illustrate graphically results obtained using the conditions indicated.

FIG. 2 shows the incorporation of (o) radioactive 100 μM d-GpGp[³H]T and (o) 100 μM d-(T$_p$)$_8$[³H]T; with time into transformed Syrian hamster embryonic fibroblasts growing in monolayer at 37° C. The incorporation is approximately linear for the first hour and begins to level off after 1.5 h. The concentration of radioactivity inside the cells is ~117 μM after 1.5 hr assuming a cell volume of 1.5 μL/10⁶ cells.

Cells were incubated with 25 μM d-GpGp[³H]T for 18 h. The medium was removed, and the cells were washed with phosphate buffer and then lysed with NaDodSo₄. Approximately 30% of the total radioactivity from the lysate was found in Cl₃AcOH-precipitable material. The DNA was precipitated from the lysate and digested with deoxyribonuclease and snake venom phosphodiesterase. The culture medium, the DNA-free lysate, and the DNA digest were each examined by paper chromatography. Only intact d-GpGp-[³H]T was found in the medium. Radioactivity corresponding to d-GpGp[³H]T (70%) and to [³H]TTP, [³H]T and [³H]DNA (30%) were found in the cell lysate.

Similar uptake studies were carried out with d-Ap[³H]T and with a series of oligothymidylate analogues, d-(Tp)$_n$[³H]T (n=1, 4, and 8). The rates and extents of uptake of these analogues were very similar to that of d-GpGp[³H]T (FIG. 1). Examination of the culture medium and cell lysate after overnight incubation with these oligonucleotides gave results similar to those found for d-GpGp[³H]T.

Effects of Oligodeoxyribonucleoside Methylphosphonates on Colony Formation by Bacterial and Mammalian Cells The effects of selected oligodeoxyribonucleoside methylphosphonates on colony formation by *E. coli* B, transformed Syrian hamster fibroblast (BP-6), and transformed human fibroblast (HTB 1080) cells are summarized in Table VII. The di-(Ap)$_n$A analogues appear to inhibit *E. coli* colony formation at high concentrations (160 μM). However, no inhibitory effects on the incorporation of [³H]leucine into cellular protein or [³H]thymidine into cellular DNA could be detected in the presence of these compounds.

TABLE VII
Effects of Oligonucleoside Methylphosphonates on Colony Formation by Bacterial and Mammalian Cells in Culture

| | % inhibition[a] | | | |
|---|---|---|---|---|
| | *E. coli* B | | BP-6, | HBT 1080, |
| oligomer | 50 μM | 160 μM | 50 μM | 50 μM |
| d-ApT | 4 | 5 | 5, 16[b] | 12 |
| d-ApA | 8 | 58 | 6, <1[b] | 5 |
| d-ApApA | 3 | 44 | 29 | 31 |
| d-ApApApA | 19 | 78 | 36 | 19 |
| d-GpGpT | 7 | 11 | 7 | 9 |

[a]The results are the average of two or three experiments. Each experiment consisted of tow plates (bacterial cells) or three plates (mammalian cells). The average variation is ±3% in percent inhbiition. The cells were treated with and grownin the presence of the oligomer at 37° C.
[b]The percent inhibition of isomers 1 and 2, respectively.

Colony formation of both transformed hamster and human cells are inhibited to various extents by the oligonucleoside methylphosphonates. Both the hamster and human cells appear to be affected to a similar extent by a given analogue. It appears in the case of d-ApA that each diastereoisomer exerts a different inhibitory effect on the growth of the hamster cellse. As in the case of *E. coli*, no inhibition of cellular protein synthesis could be detected.

The complexes formed by the oligodeoxyadenosine analogues with poly(U) and poly(dT) are more stable than similar complexes formed by either oligoribo- or oligodeoxyribonucleotides. This is apparently due to decreased charge repulsion between the nonionic backbone of the analogue and the negatively charged complementary polynucleotide backbone. With the exception of r-ApApApA (Table IV), the stability of the complexes formed with poly(dT) are slightly higher than those formed with poly(U). The lower stability of the (r-ApApA-pA)-2[poly(dT)] complex is also reflected at the polymer level. Thus, under the conditions of the experiments described in Table IV, it is found that the $T_m$ of poly(rA).2[poly(rU)] is 83° C. while the $T_m$ of poly(rA).2[poly(dT)] is 59° C.

It is believed that the anticodon loop of tRNA$_{E.\ coli}$-$^{Lyn}$ is part of the synthetase recognition site. Thus, inhibition of aminoacylation by the oligodeoxyribonucleoside methylphosphonates could result from the reduction in the affinity of the synthetase for tRNA$^{Lys}$-oligonucleotide complexes. The greater inhibition observed with d-ApApApA vs. the diesters, d-ApApApA or r-ApApApA, may result from greater binding of the analogue to the anticodon loop or to the decreased ability of the synthetase to displace the nonionic oligonucleotide analogue vs. the phosphodiester oligomers from the anticodon loop. Alternatively, oligomer binding to the anticodon loop could induce a conformational change in the tRNA, leading to a lower rate and extent of aminoacylation. Such conformational changes have previously been detected when r-ApApApA binds to tRNA$_{E.\ coli}$$^{Lys}$.

None of the oligomers have any effect on the aminoacylation of tRNA$_{rabbit}$$^{Lys}$ in a cell-free system. Since the anticodon regions of tRNAs from bacterial and mammalian sources probably are similar, the oligo(A) analogues are expected to interact with the anticodon region of both tRNA$^{Lys}$'s. The failure to observe inhibition of aminoacylation of tRNS$_{rabbit}$$^{Lys}$ in the presence of these oligo(d-A) analogues suggests that there may be a difference between the interaction of the lysine aminoacyl synthetase with tRNA$^{Lys}$ from E. coli and from rabbit systems or a difference between the structure of these two tRNA$^{Lys}$'s in response to the binding of oligo(d-A) analogues.

The trimer, dGpGpT, inhibits both phenylalanine and lysine aminoacylation at 0° C. but has little effect on leucine aminoacylation. The aminoacyl stems of both tRNA$_{E.\ coli}$$^{Lys}$ and TRNA$_{E.\ coli}$$^{Phe}$ terminate in a G—C base pair between nucleotides 1 and 72, while a less stable G—U base pair is found at this position in tRNA$_{E.\ coli}$$^{Leu}$. Thus the observed differences in inhibition of aminoacylation by d-GpGpT may reflect differences in the ability of this oligomer to bind to the different —ACC— ends of the various tRNAs.

Inhibition of lysine aminoacylation by dGpGpT is very temperature sensitive and parallels the decrease in binding to tRNA with increasing temperature. This behavior of d-GpGpT contrasts that of the ethyl phosphotriester G$_p$$^m$(Et)G$_p$$^m$(Et)U. Although both oligomers can potentially interact with the same sequences in tRNA, the ethyl phosphotriester binds more strongly and more effectively inhibits aminoacylation. The differences in binding ability may be due to overall differences in the conformation of the backbones of these oligomers.

The oligodeoxyribonucleoside methylphosphonates effectively inhibit polyphenylalanine synthesis in cell-free systems derived from both E. coli and rabbit reticulocytes. In the E. coli system, the extent of inhibition by the oligodeoxyadenosine analogues parallels the $T_m$ values of the oligomers with poly(U). The tetramer, d-ApApGpA, which would have to form a G—U base pair with poly(U), was 4.5-fold less effective than d-ApApApA. These results suggest that the oligomers inhibit polypeptide synthesis as a consequence of forming complexes with the poly(U) message. A similar inhibitory effect by poly(dA) on the translation of poly(U) has previously been observed. It is unlikely that inhibition results from nonspecific interaction of the methylphosphonates with protein components of the translation systems. In the E. coli system, poly(A) translation is inhibited to a lesser extent than is translation of poly(U), while in the reticulocyte system, no inhibition of globin mRNA translation is observed.

The data indicate that the magnitude of inhibition of poly(U)-directed polypeptide synthesis in the E. coli system does not reflect proportionally the ability of the oligomer to bind to poly(U). Although the oligomer pairs d-ApApA/d-ApA-pApA and d-ApApApA/r-ApApApA form complexes with poly(U) which have very similar $T_m$ values (see Table IV), in each case the methylphosphonate analogues inhibit 5.5-6.5 times better than do the diesters. This stronger inhibitory effect could result from a decreased ability of the ribosome to displace the nonionic oligodeoxyribonucleoside methylphosphonates from the poly(U) message, or, alternatively, there may be a degradation of the oligonucleotides (phosphodiesters) by nucleases in the cell-free translation systems but not the corresponding phosphonate analogues.

Experiments with radioactively labeled oligonucleotide methylphosphonates show that these analogues are taken up by mammalian cells growing in culture. The extent of uptake is consistent with passive diffusion of the oligomer across the cell membrane. Both d-Tp[$^3$H]T and d-(Tp)$_8$[$^3$H]T are taken up to approximately the same extent, which suggests that there is no size restriction to uptake over this chain length range. This behavior is in contrast to results obtained with E. coli B cells.

Examination of lysates of mammalian cells exposed to labeled oligomers for 18 h showed that ~70% of the labeled thymidine was associated with intact oligomer with the remainder found in thymidine triphosphate and in cellular DNA. These observations indicate that the oligodeoxyribonucleoside methylphosphonates, which are recovered intact from the culture medium, are slowly degraded within the cell. Failure to observe shorter oligonucelotides and the known resistance of the methylphosphonate linkage to nuclease hydrolysis suggests that degradation may result from cleavage of the 3+-terminal [$^3$H]thymidine N-glycosyl bond with subsequent reutilization of the thymine base.

The uptake process of the oligonucleoside methylphosphonates is quite different from that of previously studied oligonucleotide ethylphosphotriesters. In the case of the phosphotriester G$_p$$^m$(Et)G$_p$$^m$(Et)[$^3$H]U, the oligomer is rapidly taken up by the cells and is subsequently deethylated. Further degradation to smaller oligomers is then observed, presumably as a result of nuclease-catalyzed hydrolysis of the resulting phosphodiester linkages. Approximately 80% of the oligomer is metabolized within 24 h. Although the rate of uptake of the phosphotriester d-Gp(Et)Gp-(Et)[$^3$H]T is similar to that of the phosphonate d-GpGp[$^3$H]T, examination of the cell lysate showed extensive degradation of the phosphotriester analogue. The relatively long half-lives of the oligodeoxyribonucleoside methylphosphonates could be of considerable value in pharmacological applications of these oligonucleotide analogues.

The effects of these analogues on cell colony formation confirmed that the methylphosphonates are taken up by both mammalian and bacterial cells. As noted, all the oligomers tested inhibited colony formation of both cell types to various extents.

EXAMPLE 2

This example illustrates the invention using a series of oligodeoxyribonucleoside methylphosphonates with base sequences d(ApGpGp), d(ApGpGp)₂, and d[(ApGpGp)₂T] which are complementary to the Shine-Dalgarno sequence (—A—C—C—U—C—C—U) found at the 3' end of bacterial 16 S rRNA. The base complementary interaction between the 3'-terminal polypyrimidine sequence —C—C—U—C—C—U— of 16 S rRNA is the ribosome and the polypurine sequence —A—G—G—A—G—G— preceding the initiator triplet of mRNA is believed to be an essential recognition step in the initiation of protein synthesis in *Escherichia coli*. Accordingly, by binding the 3' end of 16S rRNA, using an oligodeoxyribonucleoside according to the invention, it should be possible to inhibit protein synthesis caused by the bacteria. This inhibition is shown by a reduction of colony formation in treated cells.

As in the case of Example 1, commercially available materials were also used in this example. For instance, 2'-deoxyadenosine, 2'-deoxyguanosine, and thymidine were obtained from P-L Biochemicals and poly(U) and poly(A) were obtained from Sigma. MS-2 RNA is a product of Miles. [³H]Thymidine (101 Ci/mmol; 1 Ci=3.7×10¹⁰ becquerels), [³H]lysine (54 Ci/mmol), [³H]leucine (55 Ci/mmol), and [³H]phenylalanine (35 Ci/mmol) were obtained from ICN. [³H]Uridine (25 Ci/mmol), ³H-labeled L-amino acid mixture, and the rabbit reticulocyte cell-free protein synthesizing systems were obtained from New England Nuclear.

The deoxyribooligonucleoside methylphosphonates used in this example, i.e. the compound d-[ApGpGpApGpGp)T] and its intermediates, d-(ApGpGp) and d(ApGpGp)₂, were synthesized, purified and isolated in the manner described in Miller et al (1979) Biochemistry 18, 5134–5143.

The base ratios of the products were determined by depurination with 80% acetic acid (5 hr at 60° C.). The resulting bases were separated by high-performance liquid chromatography on a reverse-phase Partisil ODS-2 column (Whatmann) with a 5–20% acetonitrile gradient in water (50 ml, total). Adenine and guanine had retention times of 5.6 and 2.0 min, respectively. Under the same conditions, d(ApGpGp) and d(ApGpGpApGpGp) had retention times of 12.5 and 18.0 min, respectively. The ratio of bases was determined from the area of the peaks. For d(ApGpGp) and d(ApGpGpApGpGp), the ratio of adenine to guanine was 1:1.9 and 1:1.95, respectively. The reaction conditions and yields in the preparation of the deoxyribooligonucleoside methylphosphonates are shown below in Table VIII. Because of the trinucleotide sequence d(A—G—G) is repeated in the heptamer, condensation of the trinucleotide blocks was considered to be more favorable than the stepwise addition of mononucleotides. The fully protected heptamer was prepared by condensing T(OAC) or [³H]T(OAC) with the protected hexamer (data not shown).

TABLE VIII

Preparation of protected oligodeoxyribonucleoside methylphosphonates

| 3'-Methylphosphonate Component | mmol | 5'-OH Component | mmol | MST mmol | Product Name | Yield mmol | Yield % |
|---|---|---|---|---|---|---|---|
| d([(MeO)₂Tr]ibuGp) | 2.77 | d(ibuGpCNEt) | 2.99 | 6.64 | (ibuGpibuGpCNEt) | 0.75 | 27 |
| d([(MeO)₂Tr]bzAp) | 1.1 | d(ibuGpibuGpCNEt) | 0.725 | 2.2 | d([(MeO)₂Tr]bzApibuGpibuGpCNEt) | 0.15 | 31 |
| d([(MeO)₂Tr]bzAp-ibuGpibuGp) | 0.033 | d(bzApibuGpibuGpCNEt) | 0.04 | 0.132 | d([MeO)₂Tr]bzApibuGpibuGpbzApibuGpibuGpCNet) | 0.01 | 30 |

The trimer d(ApGpGp) and hexamer d(ApGpGpApGpGp) were deblocked from d([(MeO)₂Tr]bzApibuGpibuGpCNEt) and d([MeO)₂Tr]bzApibuGpibuGpbzApibuGpibuGpCNEt), respectively, and hence obtained with the 5'-terminal methylphosphonate group. Reactions carried out on a small scale (<0.01 mmol) were deblocked as such and the product was isolated by paper chromatography. The purity of the oligomers was examined mainly by high-performance liquid chromatography and paper chromatography. The UV spectral properties and paper chromatographic mobilities are given in Table IX.

TABLE IX

UV spectra and chromatographic mobilities of oligodeoxyribonucleoside methylphosphonates

| Oligomer | UV spectra* λ max., nm | μ min., nm | $\epsilon_{260/280}$ | $\epsilon_{max}$++ | Paper chromatography, +R$_f$ |
|---|---|---|---|---|---|
| d(ApGpGp) | 257 | 228 | 2.11 | — | 0.77 |
| d(ApGpGpT) | 257 | 229 | 2.02 | 4.19 × 10⁴ | 0.88 |
| d(ApGpGpApGpGp) | 257 | 229 | 2.11 | 6.6 × 10⁴ | 0.27 |
| d(ApGpGpApGpGpT) | 257 | 232 | 2.06 | 7.33 × 10⁴ | 0.39 |

*In water at pH 7.0.
+Run in solvent F; R$_F$ of pT. 0.41. Solvent F is n-propanol/NH₄OH/H₂O, 55:10:35 (vol/vol).
++Obtained by comparing the absorbance of a solution of the oligomer in water in pH 7.0 to that of the same solution at pH 1.0. The oligomer extinction coefficient was calculated from the observed hyperchromicity of the oligomer at pH 1.0 by using the following coefficients: dA at pH 1.0, 14.1 × 10¹, dG at pH 1.0, 12.3 × 10³.

The interaction of d(ApGpGpApGpGp[³H]T) and d(ApGpGp[³H]T) with 70S ribosomes was studied by equilibrium dialysis. The heptamer has a high apparent association constant which decreases with increasing temperature (4.67×10⁵M⁻¹ at 0° C.; 1.72×10⁵M⁻¹ at 22° C.; 2.0×10⁴M⁻¹ at 37° C.). As expected, the tetramer, which has only four bases complementary to the 3' end of 16S rRNA, has a proportionately lower association constant (1.44×10⁴M⁻¹ at 22° C.).

Dialysis experiments were performed in 30-μl plexiglass chambers separated by a dialysis membrane. The equilibration buffer contained 60 mM Tris.HCl (pH 7.5), 120 mM NH₄Cl, 6 mM MgCl₂, 0.6 mM dithiothreitol, 0.6 mM GTP, 200 pmol of *E. coli* B ribosomes, and 135-175 pmol of ³H-labeled deoxyribooligonucleoside methylphosphonates. The chambers were equilibrated at the desired temperature for 2 days before measurement.

A cell-free protein-synthesizing system and 70S ribosomes from *E. coli* B were prepared according to the method of Nirenberg (1963, Methods Enzymal. 6, 17-23). Cell-free protein synthesis in a rabbit reticulocyte system was performed by using a cell-free translation system purchased from New England Nuclear (lot J1157AW). For the translation of globin mRNA, the reactions were run in 25.0 μl of buffer containing 2 μl of translation mixture, 2 μg of globin mRNA, 79 mM potassium acetate, 0.65 mM magnesium acetate, 0-100 μM oligomer, and 14 μM [³H]leucine. Reactions were initiated by addition of 5 μl of reticulocyte lysate. Aliquots (4 μl) were removed at various times and added to 0.1 ml of bovine serum albumin (100 μg) solution. The protein was precipitated by heating with 1 ml of 10% trichloroacetic acid at 70° C. filtered on G/F filters, and assayed for radioactivity in Betafluor.

*E. coli* ML 308-225 cells were grown at 37° C. in minimal salt medium supplemented with 1% glucose. *E. coli* B cells were grown in M9 medium as described in the literature (Bolle et al, 1968, J. Mol. Biol. 33, 339-362). Protein synthesis and RNA synthesis were carried out in cells grown to midlogarithmic phase ($\approx 5.0 \times 10^8$ cells per ml). Aliquots (50 μl) of cells were preincubated with 15 μl of medium or medium containing the compounds for 1-2 hr at 22° C. *E. coli* ML cells were transferred to a water bath maintained at 10° C. After 10 min, 3 μl of [³H]uridine (100 μCi/ml) or 3 μl of [³H]leucine (50 μCi/ml) was added; then 15-μl aliquots were withdrawn at 0, 5, 10 and 20 min and added to 200 μl of lysing buffer (2.0% NaDodSO₄/0.02M EDTA) and heated at 70° C. for 20 min. For protein synthesis experiments, bovine serum albumin (100 μg) and 20% trichloroacetic acid (1 ml) were added and the solution was heated at 70° C. for 15 min. Then the solution was filtered; the filter was then washed and assayed for radioactivity. For RNA synthesis experiments, cold 5% trichloroacetic acid was added after lysis of the cells, and the solution was filtered without heating. The final concentration of oligomers in these experiments was 100 μM.

For determination of colony formation, *E. coli* ML 308-225 cells were incubated for 2 hr in 100 μl of medium containing 75-160 μM of oligonucleoside methylphosphonate. The solution was then diluted to 1.0 ml with the medium. To 0.9 ml of this solution, 2.0 ml of 0.5% bactoagar was added at 37° C. and the solution was poured onto 100-mm plates containing 1.5% bactoagar. After solidification, the plates were incubated at 37° C. for 36 hr, and the colonies were counted. The final concentration of the oligomers on the plate was 2.6-5.5 μM.

In vitro aminoacylation experiments were done as described by Barrett et al (1974), Biochemistry 13, 4898-4906.

Growth experiments were done by treating 15 μl of cells ($\approx 1 \times 10^8$ cells per ml) in 15 μl of medium (control) or medium containing 150 μM of the compounds at 37° C. Aliquots (4 μl) were withdrawn at different time intervals and appropriately diluted. The number of cells was determined by using a Hausser counting chamber and a Zeiss phase-contrast microscope.

The effects of the oligomers on cell-free protein synthesis in *E. coli* B system are summarized in Table X.

TABLE X

Effect of deoxyriboligonucleoside methylphosphonates on cell-free protein-synthesizing system from *E. coli* B

| Oligomer | Conc., μM | Inhibiiton, % Poly (U)* 22° C. | Poly (U)* 37° C. | Poly (A)+ 22° C. | Poly (A)+ 37° C. | MS-2 RNA 22° C. |
|---|---|---|---|---|---|---|
| d(ApGpGp) | 100 | 8 | 0 | 0 | 0 | 5 |
| d(ApGpGpT) | 100 | — | — | — | — | 0 |
| d(ApGpGpApGpGp) | 12.5 | — | — | — | — | 45 |
|  | 25 | 0 | 0 | 0 | 0 | 75 |
|  | 50 | 19 | 0 | 29 | 14 | 88 |
|  | 100 | 39 | 18 | 80 | 27 | — |
| d(ApGpGpApGpGpT) | 25 | 0 | 0 | 0 | 0 | 77 |
| d(CpCpApApGpCp)++ | 100 | — | — | — | — | 21 |

*At 260 μM in UMP residues
+At 225 μM in AMP residues
++p = p-chlorophenylphosphate In general, the hexamer and heptamer exhibited inhibitory activities but the trimer and tetramer did not. Poly-(U)-directed polyphenylalanine synthesis and poly(A)-directed polylysine synthesis were not inhibited appreciably by hexamer and heptamer at 37° C. The inhibition was greater at 22° C. than at 37° C. At higher concentrations, the hexamer inhibited polylysine synthesis directed by poly(A) more effectively than polyphenylalanine synthesis directed by poly(U). Whereas d-(ApGpGp) and d-(ApGpGpT) did not cause appreciable inhibition of the translation of MS-2 RNA in the *E. coli* system, d-(ApGpGpApGpGp) and d-(ApGpGpApGpGpT) were effective inhibitors in dose-dependent manner, even at low concentrations. As a negative control for sequence specificity, d-(CpCpApApGpCp-chlorophenylphosphate), a hexamer not complementary to the 3' end of 16S rRNA, was used. This oligomer was found to be much less effective in inhibiting translation of MS-2 RNA in the *E. coli* system. In contrast to their effects on the *E. coli* system, both d-(ApGpGpApGpGp) and d-(ApGpGpApGpGpT), which are not complementary to the 3' end of eukaryotic 18S rRNA, did not have appreciable inhibitory effects on the translation of globin mRNA in a cell-free reticulocyte system (at 100 μM and 22° C., 16% and 17%, respectively).

The effects of deoxyribooligonucleoside methylphosphonates on the colony formation by *E. coli* B, *E. coli* ML 308-225, and transformed human cells (HTB 1080) as well as the effects of these analogues on cellular protein synthesis in *E. coli* B and *E. coli* ML-308-225 were investigated. Oligomers d(ApGpGp), d(ApGpGpApGpGp), and d(ApGpGpApGpGpT) inhibited colony formation by E. coli ML 308–225 cells effectively (Table XI).

TABLE XI

Effect of deoxyribooligonucleoside methylphosphonates on colony formation

| Oligomer (at 75 μM) | Inhibition, % | | |
|---|---|---|---|
| | E. coli ML 308-225* | E. coli B* | Human cells HBT 1080[30] |
| d(ApGpGp) | 75–98 | 0 | — |
| d(ApGpGpApGpGp) | 78–97 | 0 | — |
| d(ApGpGpApGpGpT) | 67–97 | 0 | 10 |
| d(ApGpGpT) | 0 | 0 | — |
| d(GpGpT) | 5 | — | — |

*At either 22° C. or 37° C.
*At 37° C.

These analogues had virtually no effect on colony formation by E. coli B cells and only a small inhibitory effect on colony formation by transformed human cells.

Results of the study on cellular protein synthesis by E. coli ML 308–225 support the observation on the colony formation by these two strains of bacteria. The rates of incorporation, by E. coli ML 308–225 cells, of axogenous [$^3$H]leucine into hot trichloroacetic acid-precipitable material and of [$^3$H]uridine into cold trichloroacetic acid-precipitable material were found to be quite rapid at 37° C. and 22° C.; however, the incorporation leveled off in 5 min at these temperatures. Hence, incorporation of [$^3$H]leucine and [$^3$H]uridine by this E. coli mutant were studied at a lower temperature (10° C.). The incorporation was linear up to 10 min at this temperature. d(ApGpGpApGpGpT) inhibited protein synthesis by E. coli ML 308–225 but not by E. coli B. Some variation in the extent of inhibition was observed between experiments, and the inhibition was found to be in the range of 20–45%. Under the same experimental conditions, d(ApGpGpApGpGpT) had no effect on RNA synthesis as measured by [$^3$H]uridine incorporation. d(ApGpGpT) has no effect on either protein synthesis (Table XI) or RNA synthesis.

Figure 3:
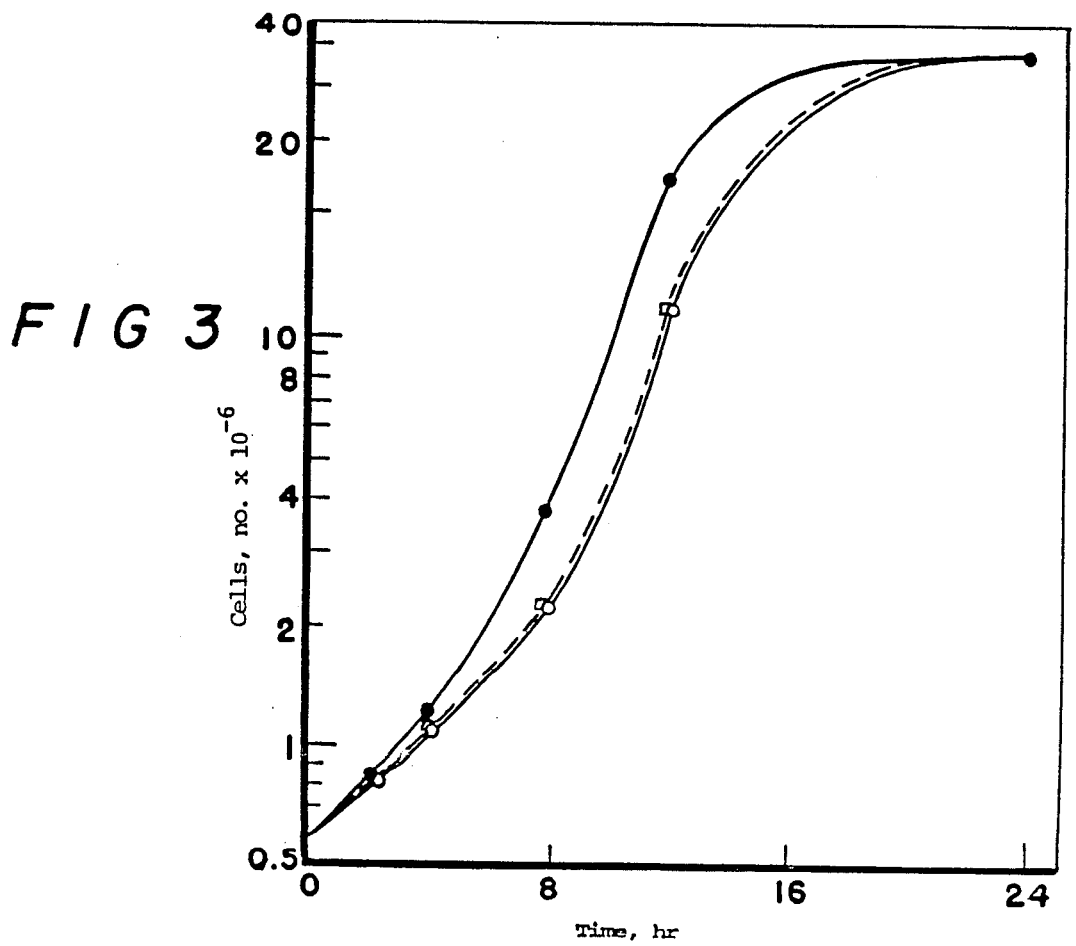

In addition to the studies on colony formation, experiments were done on the growth of E. coli ML 308–225 in mass culture in the presence of the oligonucleotide analogues. FIG. 3 shows the results obtained, o representing an untreated or control culture; O and □—□ representing cultures including 150 μM d(ApGpGp) and 150 μM d(ApGpGp)$_2$T, respectively. There was no inhibition of growth during the first 4 hr (FIG. 3). At the rapid growth period between 4 and 12 hr, the growth of the treated culture was inhibited up to 50% in the presence of either trimer or heptamer. At the end of this growth period, 24 hr after initiation of the culture, the treated and untreated cultures had approximately the same number of cells.

The results shown in Example 2 indicate that the two phosphonate analogues, d(A]GpGp[$^3$H]T) and d(A]GpGpApGpGp($^3$H]T), which are complementary to the 3' end of 16S rRNA, exhibit high affinity for 70S ribosomes as studied by equilibrium dialysis. Earlier studies on the interation of a pentanucleotide (G—A—dG—U) with E. coli 30S and 70S ribosomes have shown that this pentamer specifically binds to a site on the 30S subunit (Eckhardt et al, 1979, J. Biol. Chem. 254, 1185–1188). Hence, it is very likely that the observed binding of the tetramer and helptamer analogus with 70S ribosimes is due to their formation of complexes with the complementary regions at the 3' end of 16S rRNA. This view is further supported by studies on the effect of these analogues on cell-free protein synthesis. Both the hexamer and heptamer effectively inhibit the translation of MS-2-RNA in the E. coli cell-free system while having a much lower inhibitory effect on the translation of poly(U) and poly(A). The in vitro aminoacylation of tRNA$_{coli}$ is not inhibited by these oligomers, suggesting that the inhibition of aminoacylation of tRNAs does not play a role in the inhibition of translation of MS-2RNA. The inhibition observed in the E. coli system, therefore, is most likely at the ribosome site. Because the synthetic mRNAs, unlike natural mRNAs, lack specific initiation sites, the results also support the conclusion that the inhibition of translation of MS-2 RNA may arise from competition between the oligonucleotide analogues and the homologous sequence within the preinitiator region of MS-2 RNA. The indicated results appear to be in agreement with those obtained by Taniguchi et al (1978, Nature, 275, 770–772) and Eckhardt et al, supra. These authors have observed an inhibition of formation of phage mRNA-70S ribosome initiation complex in the presence of oligonucleotides complementary to the 3' end of 16S rRNA. In contrast, no inhibition of poly(U)-dependent tRNA$^{Phe}$ binding to 70S ribosomes was found. Additional support for the base-complementary interaction of oligonucleotide analogues with the 3' end of 16S rRNA comes from the inability of these analogues to inhibit the translation of globin mRNA in a rabbit reticulocyte system. Although the 3'-end sequences of 18S rRNA and 16S rRNA are similar, 18S rRNA specifically lacks the —C—C—U—C—C—U sequence found in 16S rRNA, and hence the oligonucleotide analogues cannot form stable complexes with 18S rRNA in reticulocyte ribosomes.

Although the oligomers inhibit translation of mRNAs in the E. coli B cell-free system, these oligomers have no effect on either protein synthesis or colony formation by the intact E. coli B cells; however, as shown in Table XI, these oligomers inhibit the protein synthesis and growth of an E. coli mutant (ML 308–225). Experiments on the uptake of oligonucleotides by E. coli B cells indicate that they are permeable to d-(Ap[$^3$H]T), d-Tp[$^3$H]T, and d-TpTp[$^3$H]T but not to d-(Tp)$_4$[$^3$H]T and d-(Tp)$_8$[$^3$H]T. Thus, oligonucleoside methylphosphonates longer than 4 nucleotide units cannot enter the cell. The cutoff size limit found for oligosaccharides and oligopeptides. In contrast to E. coli B. E. coli ML 308–225 cells were permeable to d-ApGpGpApGpGp[$^3$H]T). This E. coli mutant has only small quantities of lipopolysaccharide in the outer membrane of the cell wall. The reduction in lipopolysaccharide content may increase the permeability of cell wall toward oligonucleoside methylphosphonates. Thus, the difference in the permeability of the cell walls of these two bacteria can explain why the hexamer and heptamer do not have any effect on intact E. coli B cells but inhibit protein synthesis, colony formation, and culture growth of E. coli ML 308–225.

The specific inhibitory effects of oligonucleotide analogues in the cell-free systems is also indicated by the following observations at the intact cellular level (Table XI): (i) The oligonucleotide analogues inhibit protein synthesis and growth of E. coli ML 308-225 cells but have little of no effect on human cells, (ii) Although d-(ApGpGpApGpGp) and d-(ApGpGpApGpGpT) inhibit colony formation by E. coli ML 308–225, d-(ApGpGpT) has no effect; and (iii) d-(ApGpGpApGpGpT) inhibits protein synthesis without concurrent inhibition of RNA synthesis.

The use of the nuclease-resistant, nonionic oligonucleoside methylphosphonates which are taken up by mammalian cells according to the invention to inhibit viral protein synthesis and infection may be further exemplified by means of octamers which are complementary to: (1) the initiation codon regions of α and β globin mRNA (rabbit), and vesicular stomatitis virus (VSV) N and NS protein mRNA; (2) the donor splice junction of SV-40 T-antigen premRNA; (3) the acceptor splice junction of Herpes simplex virus-1 (HSV-1), preIE mRNA-4. It has been found that anti-globin mRNA oligonucleoside methylphosphonates (25–100 μM) serve as specific primers for reverse transcriptase and inhibit globin mRNA translation (25–70%) in reticulocyte lysates at 37° C. It has also been found that anti N-protein, according to the invention, (120–180 μM) inhibits synthesis of N, NS, M, G and L proteins (50–80%) in VSV-infected mouse L-cells, but does not appear to inhibit L-cell protein synthesis. Anti-T-antigen oligonucleoside methylphosphonate (100 μM) inhibits T-antigensynthesis (19%) in SV-40 infected BSC-40 cells but does not inhibit cellular protein synthesis. Additionally, anti-HSV-1 ONMP (300 μM) completely inhibits immediate early protein synthesis in HSV-1 infected Vero cells and reduces virus titer $10^3$-fold, but has no effect on Vero cell viability. Thus, presumably through duplex formation with complementary targeted regions of RNA, sequence-specific oligonucleoside methylphosphonate may be used, according to the invention, to specifically control viral function and replication within the indicated infected cells. This control involves inhibiting translation of viral mRNA as in the case of vesicular stomatitis virus or processing (splicing) of virus pre-mRNA as in the case of SV-40 or Herpes virus.

The sequence of the oligomer referred to in the preceding paragraph in connection with the Herpes virus is:

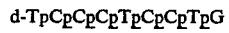

d-TpCpCpCpTpCpCpTpG where
p̲=methylphosphonate linkage
p=phosphodiester linkage.

It is noted that Herpes virus Type 1 and Type 2 are propogated in Vero cells. The indicated methylphosphonate oligomer has no apparent effect on the growth of these cells up to a concentration of 300 μM. This has been determined by visual examination of the cells under the microscope. However, the oligomer has been found to inhibit the growth of both Herpes simplex Type 1 and Herpes simplex Type 2 virus in Vero cells at a concentration of 300 μM. The virus titer is reduced 2 log units, i.e. 99% inhibition for Type 1 virus and approximately 1 log unit, i.e. ~90% inhibition for the Type 2 virus. This oligomer inhibits production of virus proteins as determined by an immunoflourescene assay. Virus proteins (from either Type 1 or Type 2 virus) are not observed when infected cells are treated with the oligomer at 300 μM concentration. The oligomer, therefore, offers the prospect of providing an effective treatment against the Herpes virus.

The temporary inhibition of the growth of *E. coli* ML 308–225 cells in mass culture by the trimer and heptamer (FIG. 1) is in agreement with the expectation that the oligomers may not have caused a permanent damage to the functioning of ribosomes. The cells can overcome this inhibition by synthesizing more ribosomes, or the inhibitory effect of the oligomers will not be detectable when the capacity of the ribosomes for protein synthesis is no longer the factor limiting growth.

In summary, the results set forth above indicate that it is possible by using an oligonucleotide methylphosphonate analogue which has a sequence complementary to a bacterial, viral or mammalian nucleic acid of defined sequence to inhibit or otherwise control such nucleic acid and its function within a living cell and without undesirably affecting the normal function of the cell. The invention consequently offers the possibility of controlling or inhibiting bacteria, viruses and malfunctioning cells in or adjacent to normal mammalian or animal cells by appropriately binding their vital nucleic acids (the vital foreign nucleic acid) with nonionic oligonucleotides which are complementary thereto.

It will be recognized that various modifications may be made in the invention without departing from the scope thereof as set out in the appended claims herein.

We claim:

1. A method for inhibiting the Herpes simplex virus (type 1 and type 2) in a host in need of such treatment which comprises binding the said virus in said host with an effective amount of a nonionic oligonucleoside alkyl or arylphosphonate which is complementary to the base sequence of said virus.

2. The method of claim 1 wherein the oligonucleotide alkyl or arylphosphonate is an octamer.

3. The method of claim 1 wherein the phosphonate is an oligonucleoside methyl phosphonate.

4. The method of claim 1 wherein the oligonucleoside alkylphosphonate has the formula:

d-TpCpCpTpCpCpTpG where
p̲=methylphosphonate linkages
p=a phosphodiester linkage.

UNITED STATES PATENT AND TRADEMARK OFFICE
CERTIFICATE OF CORRECTION

PATENT NO. : 4,757,055

DATED : July 12, 1988

INVENTOR(S) : Miller et al

It is certified that error appears in the above-identified patent and that said Letters Patent is hereby corrected as shown below:

Column 1, between the Title and the heading "RELATED APPLICATIONS", please insert:

--The invention described herein was made in the course of work under a grant (NIH GM166066-12) from the Department of Health and Human Services.--.

Signed and Sealed this

Twenty-first Day of September, 1993

Attest:

BRUCE LEHMAN

Attesting Officer

Commissioner of Patents and Trademarks